(12) United States Patent
Epstein et al.

(10) Patent No.: US 6,921,380 B1
(45) Date of Patent: Jul. 26, 2005

(54) COMPONENT MIXING CATHETER

(75) Inventors: Gordon Howard Epstein, Fremont, CA (US); Mitchell E. Levinson, Pleasanton, CA (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/408,091

(22) Filed: Sep. 29, 1999

Related U.S. Application Data

(60) Provisional application No. 60/102,636, filed on Oct. 1, 1998.

(51) Int. Cl.[7] .......................... A61M 37/00; A61M 5/00; B67D 5/52

(52) U.S. Cl. .................... 604/82; 604/191; 222/137; 606/214

(58) Field of Search ................................. 604/181, 187, 604/191, 82, 83, 89, 218; 606/213, 214; 222/137, 135, 309

(56) References Cited

U.S. PATENT DOCUMENTS

| | | | |
|---|---|---|---|
| 786,985 | A | 4/1905 | Nicholis |
| 1,206,126 | A | 11/1916 | Mitsch |
| 1,889,425 | A | 11/1932 | Sorensen |
| 2,112,160 | A | 3/1938 | Johnson |
| 2,158,593 | A | 5/1939 | Scrimgeour |
| 2,576,766 | A | 11/1951 | Sokolik |
| 2,812,765 | A | 11/1957 | Tofflemire |
| 3,065,749 | A | 11/1962 | Brass |
| 3,071,402 | A | 1/1963 | Lasto |
| 3,144,868 | A | 8/1964 | Jascalevich |
| 3,159,312 | A | 12/1964 | Sciver II |

(Continued)

FOREIGN PATENT DOCUMENTS

| | | |
|---|---|---|
| DE | 26 05 005 | 2/1976 |
| DE | 8133489 | 5/1982 |
| DE | 196 36 622 C1 | 6/1998 |
| EP | 0 037 393 | 4/1981 |
| EP | 0 156 098 | 12/1984 |
| EP | 0 302 411 | 7/1988 |
| EP | 0 424 068 A2 | 10/1990 |
| EP | 0538 174 A1 | 9/1992 |
| EP | 0 669 100 A1 | 2/1995 |
| EP | 0 800 361 B1 | 12/1995 |
| EP | 0738 498 A1 | 4/1996 |

(Continued)

OTHER PUBLICATIONS

McCarthy et al., Barium Impregnated Fibrin Glue: Application to a Bleeding Duodenal Sinus, Mayo Clinic Pros., vol. 62, pp. 317 319, 1987.
PCT International Search Report, PCT/US98/07488, Jul. 8, 1998.
PCT International Search Report, PCT/US98/07846, Jul. 18, 1998.
U.S. Appl. No. 09/315702, filed May 1999, Levinson et al.

Primary Examiner—Sharon Kennedy
(74) Attorney, Agent, or Firm—Jeffrey C. Nichols

(57) ABSTRACT

A multi-component sealant applicator comprises a dual catheter for delivering sealant. Each catheter communicates with one of a pair of fluid sealant agent sources and comprises a mixing volume within the dual catheter for mixing multiple components of a multi-component sealant prior to discharge from a distal end of the catheter and a clearing system to clear undesired material from the mixing volume or the vicinity of the mixing volume, wherein one catheter is mounted for longitudinal movement within the other and the inner catheter is usable as a plunger to remove clogs. The catheter may comprise a reciprocal drive mechanism proximally coupled with the dual catheter to move one catheter longitudinally with respect to the other. The drive mechanism may comprise a ratchet and pawl.

4 Claims, 7 Drawing Sheets

U.S. PATENT DOCUMENTS

| | | |
|---|---|---|
| 3,179,107 A | 4/1965 | Clark |
| 3,188,056 A | 6/1965 | Trumbull |
| 3,208,145 A | 9/1965 | Turner |
| 3,223,083 A | 12/1965 | Cobey |
| 3,469,582 A | 9/1969 | Jackson |
| 3,594,980 A | 7/1971 | Diehl |
| 3,625,221 A | 12/1971 | Corbett |
| 3,626,928 A | 12/1971 | Barringer |
| 3,645,497 A | 2/1972 | Nyboer |
| 3,672,544 A | 6/1972 | Marand |
| 3,737,106 A | 6/1973 | Arnold et al. |
| 3,767,085 A | 10/1973 | Cannon |
| 3,771,522 A | 11/1973 | Waysilk et al. |
| 3,790,080 A | 2/1974 | Babington |
| 3,828,980 A | 8/1974 | Creighton |
| 3,865,193 A | 2/1975 | Hall |
| 3,918,935 A | 11/1975 | Livingston |
| 3,949,748 A | 4/1976 | Malmin |
| 3,991,143 A | 11/1976 | Carter |
| 4,036,210 A | 7/1977 | Campbell et al. |
| 4,037,665 A | 7/1977 | Hopper |
| 4,040,420 A | 8/1977 | Speer |
| 4,043,042 A | 8/1977 | Perfect |
| 4,067,479 A | 1/1978 | Moline |
| 4,109,653 A | 8/1978 | Kozam et al. |
| 4,143,658 A | 3/1979 | Rambosek et al. |
| 4,170,232 A | 10/1979 | Khoury |
| 4,191,480 A | 3/1980 | Hiorth |
| 4,193,406 A | 3/1980 | Jinotti |
| 4,198,958 A | 4/1980 | Utsugi |
| 4,223,676 A | 9/1980 | Wuchinich et al. |
| 4,231,521 A | 11/1980 | Hermine |
| 4,236,674 A | 12/1980 | Dixon |
| 4,266,545 A | 5/1981 | Moss |
| 4,270,525 A | 6/1981 | Furihata |
| 4,294,251 A | 10/1981 | Greenwald et al. |
| 4,298,598 A | 11/1981 | Schwarz et al. |
| 4,299,221 A | 11/1981 | Phillips et al. |
| 4,325,913 A | 4/1982 | Wardlaw |
| 4,356,823 A | 11/1982 | Jackson |
| 4,359,049 A | 11/1982 | Redl et al. |
| 4,362,567 A | 12/1982 | Schwarz et al. |
| 4,377,572 A | 3/1983 | Schwarz et al. |
| 4,396,417 A | 8/1983 | Lissant |
| 4,397,640 A | 8/1983 | Haug et al. |
| 4,401,271 A | 8/1983 | Hansen |
| 4,401,272 A | 8/1983 | Merton et al. |
| 4,414,976 A | 11/1983 | Schwarz et al. |
| 4,427,650 A | 1/1984 | Stroetmann |
| 4,445,517 A | 5/1984 | Feild |
| 4,487,600 A | 12/1984 | Brownlie et al. |
| 4,504,266 A | 3/1985 | Harle |
| 4,516,442 A | 5/1985 | Davis |
| 4,519,385 A | 5/1985 | Atkinson et al. |
| 4,573,979 A | 3/1986 | Blake |
| 4,601,697 A | 7/1986 | Mammolenti et al. |
| 4,617,013 A | 10/1986 | Betz |
| 4,629,455 A | 12/1986 | Kanno |
| 4,631,055 A | 12/1986 | Redl et al. |
| 4,670,009 A | 6/1987 | Bullock |
| 4,680,026 A | 7/1987 | Weightman et al. |
| 4,690,306 A | 9/1987 | Staheli |
| 4,696,669 A | 9/1987 | Menhusen |
| 4,699,138 A | 10/1987 | Behrstock |
| 4,708,717 A | 11/1987 | Deane et al. |
| 4,728,578 A | 3/1988 | Higgins et al. |
| 4,735,616 A | 4/1988 | Eibl et al. |
| 4,735,619 A | 4/1988 | Sperry et al. |
| 4,743,229 A | 5/1988 | Chu |
| 4,759,349 A | 7/1988 | Betz et al. |
| 4,776,840 A | 10/1988 | Freitas et al. |
| 4,784,637 A | 11/1988 | Ryder et al. |
| 4,842,581 A | 6/1989 | Davis |
| 4,857,047 A | 8/1989 | Amoils |
| 4,874,368 A | 10/1989 | Miller et al. |
| 4,891,044 A | 1/1990 | Mitchell |
| 4,902,281 A | 2/1990 | Avoy |
| 4,904,238 A | 2/1990 | Williams |
| 4,925,447 A | 5/1990 | Rosenblatt |
| 4,928,884 A | 5/1990 | Smith |
| 4,935,006 A | 6/1990 | Hasson |
| 4,941,872 A | 7/1990 | Felix |
| 4,946,439 A | 8/1990 | Eggers |
| 4,969,669 A | 11/1990 | Sauer |
| 4,978,336 A | 12/1990 | Capozzi et al. |
| 4,979,942 A | 12/1990 | Wolf et al. |
| 4,981,473 A | 1/1991 | Rosenblatt |
| 5,024,615 A | 6/1991 | Buchel |
| 5,024,654 A | 6/1991 | Tyler |
| RE33,642 E | 7/1991 | Lester |
| 5,029,580 A | 7/1991 | Radford et al. |
| 5,030,201 A | 7/1991 | Palestrant |
| 5,030,202 A | 7/1991 | Harris |
| 5,030,215 A | 7/1991 | Morse et al. |
| 5,045,055 A | 9/1991 | Gonser et al. |
| 5,049,135 A | 9/1991 | Davis |
| 5,061,180 A | 10/1991 | Wiele |
| 5,104,375 A | 4/1992 | Wolf |
| 5,116,315 A | 5/1992 | Capozzi et al. |
| 5,120,305 A | 6/1992 | Boehringer et al. |
| 5,147,323 A | 9/1992 | Haber |
| 5,163,433 A | 11/1992 | Kagawa et al. |
| 5,186,714 A | 2/1993 | Boudreault et al. |
| 5,199,949 A | 4/1993 | Haber |
| 5,217,441 A | 6/1993 | Shichman |
| 5,217,465 A | 6/1993 | Steppe |
| 5,226,877 A | 7/1993 | Epstein |
| 5,240,146 A | 8/1993 | Smedley |
| 5,246,455 A | 9/1993 | Shikani |
| 5,253,785 A | 10/1993 | Haber |
| 5,271,527 A | 12/1993 | Haber et al. |
| 5,286,258 A | 2/1994 | Haber et al. |
| 5,290,552 A | 3/1994 | Sierra et al. |
| 5,295,956 A | 3/1994 | Bales et al. |
| 5,300,022 A | 4/1994 | Klapper et al. |
| 5,304,165 A | 4/1994 | Haber et al. |
| 5,314,412 A | 5/1994 | Rex |
| 5,318,782 A | 6/1994 | Weis-Fogh |
| 5,328,459 A | 7/1994 | Laghi |
| 5,348,542 A | 9/1994 | Ellis |
| 5,368,560 A | 11/1994 | Rambo et al. |
| 5,368,563 A | 11/1994 | Lonneman et al. |
| 5,376,079 A | 12/1994 | Holm |
| 5,395,326 A | 3/1995 | Haber et al. |
| 5,405,607 A | 4/1995 | Epstein |
| 5,419,769 A | 5/1995 | Devlin |
| 5,423,752 A | 6/1995 | Haber |
| 5,433,705 A | 7/1995 | Giebel et al. |
| 5,443,454 A | 8/1995 | Tanabe et al. |
| 5,447,494 A | 9/1995 | Dorsey, III |
| 5,474,540 A | 12/1995 | Miller et al. |
| 5,476,450 A | 12/1995 | Ruggio |
| 5,477,987 A | 12/1995 | Keller |
| 5,520,658 A | 5/1996 | Holm |
| 5,520,685 A | 5/1996 | Wojciechowicz |
| 5,571,081 A | 11/1996 | Adhoute |
| 5,582,596 A | 12/1996 | Fukunaga et al. |
| 5,584,815 A | 12/1996 | Pawelka |
| 5,585,007 A | 12/1996 | Antanavich et al. |
| 5,603,700 A | 2/1997 | Daneshvar |
| 5,605,255 A | 2/1997 | Reidel et al. |

| | | | | | | |
|---|---|---|---|---|---|---|
| 5,605,541 A | * | 2/1997 | Holm ............... 604/82 | 6,063,055 A | 5/2000 | Epstein et al. |
| 5,612,050 A | | 3/1997 | Rowe et al. | 6,068,203 A | 5/2000 | DeYoung et al. |
| 5,626,562 A | | 5/1997 | Castro | 6,113,571 A | 9/2000 | Zinger et al. |
| 5,643,206 A | | 7/1997 | Fischer | 6,132,396 A | 10/2000 | Antanavich et al. |
| 5,648,265 A | | 7/1997 | Epstein | 6,139,520 A | 10/2000 | McCrory et al. |
| 5,656,035 A | | 8/1997 | Avoy | 6,161,730 A | 12/2000 | Heusser et al. |
| 5,665,067 A | | 9/1997 | Linder et al. | 6,183,941 B1 | 2/2001 | Hayes |
| 5,674,394 A | | 10/1997 | Whitmore | 6,206,905 B1 * | 3/2001 | Holm et al. ............... 606/214 |
| 5,695,472 A | | 12/1997 | Wyrick | 6,234,994 B1 | 5/2001 | Zinger |
| 5,749,968 A | | 5/1998 | Melanson et al. | 6,328,229 B1 | 12/2001 | Duronio et al. |
| 5,759,169 A | | 6/1998 | Marx | 6,331,172 B1 | 12/2001 | Epstein et al. |
| 5,759,171 A | | 6/1998 | Coelho et al. | 6,394,975 B1 | 5/2002 | Epstein |
| 5,779,108 A | | 7/1998 | Barriac et al. | 6,461,325 B1 | 10/2002 | Delmotte et al. |
| 5,779,721 A | | 7/1998 | Nash | | | |
| 5,810,885 A | | 9/1998 | Zinger | | | |
| 5,814,022 A | | 9/1998 | Antanavich | | | |
| 5,814,066 A | * | 9/1998 | Spotnitz ............... 606/214 | | | |
| 5,833,652 A | | 11/1998 | Preissman et al. | | | |
| 5,879,340 A | | 3/1999 | Epstein | | | |
| 5,902,264 A | | 5/1999 | Toso et al. | | | |
| 5,964,261 A | | 10/1999 | Neuenfeldt et al. | | | |
| 5,975,367 A | | 11/1999 | Coelho et al. | | | |
| 5,976,102 A | | 11/1999 | Epstein | | | |
| 5,984,889 A | | 11/1999 | Christ | | | |
| 5,989,215 A | | 11/1999 | Delmotte et al. | | | |
| 6,007,515 A | | 12/1999 | Epstein | | | |
| 6,036,103 A | | 3/2000 | Benest | | | |

FOREIGN PATENT DOCUMENTS

| | | |
|---|---|---|
| EP | 0 738 498 A1 | 10/1996 |
| EP | 0858 775 A | 2/1998 |
| WO | WO 87/04913 | 8/1987 |
| WO | WO 95/31137 | 11/1995 |
| WO | WO 96/39212 | 12/1996 |
| WO | WO 97/28834 | 8/1997 |
| WO | WO 98/10704 | 3/1998 |
| WO | WO 99/17833 | 4/1999 |
| WO | WO 9959670 | 11/1999 |

* cited by examiner

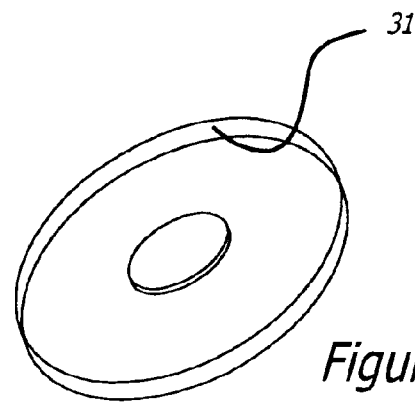
Figure 9
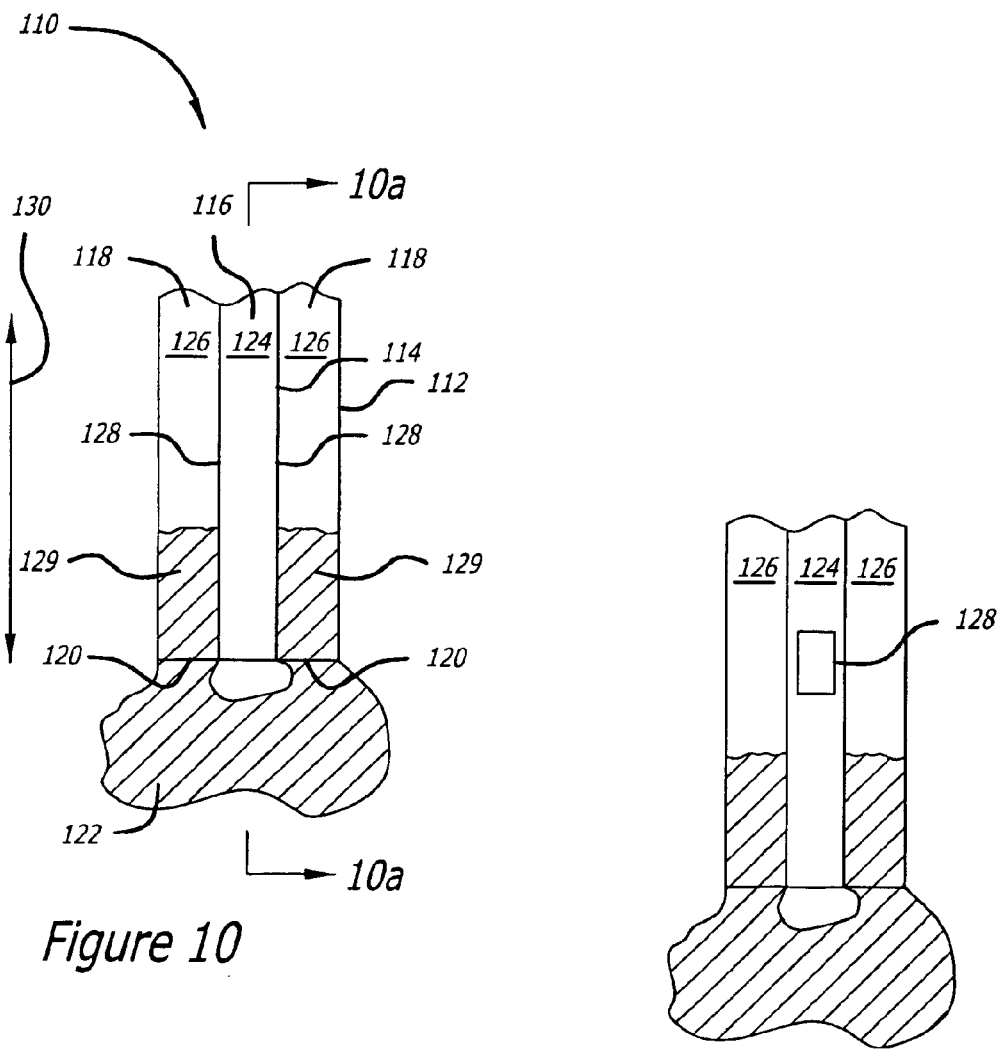
Figure 10
Figure 10a

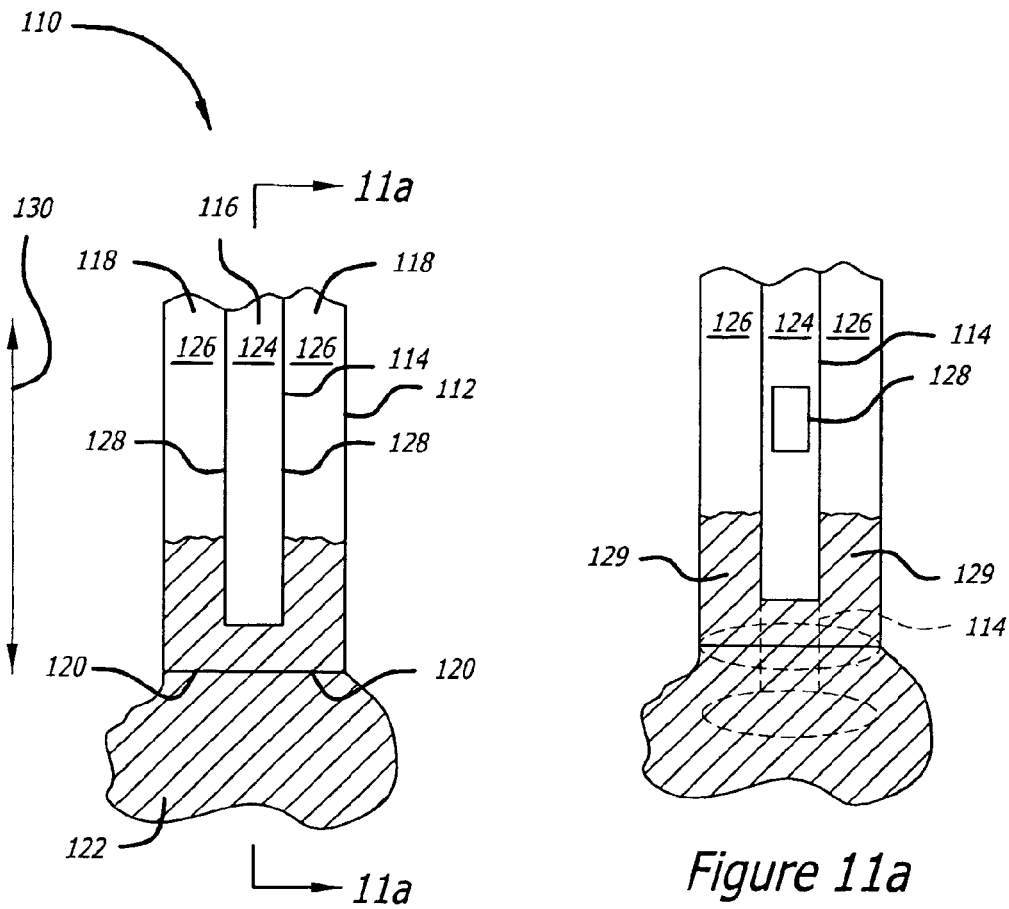
Figure 11
Figure 11a
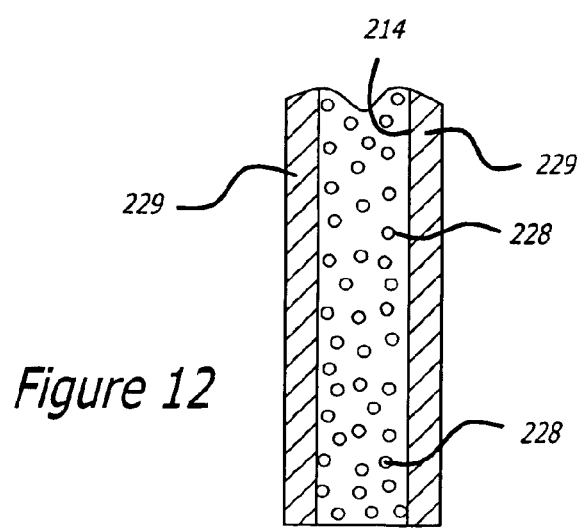
Figure 12

COMPONENT MIXING CATHETER

CROSS-REFERENCE TO RELATED APPLICATIONS

This application claims the benefit of priority from provisional application Ser. No. 60/102,636 filed Oct. 1, 1998, and entitled "IMPROVED COMPONENT MIXING CATHETER," the disclosure of which is hereby incorporated herein by reference thereto. This application discloses subject matter in the general field of commonly assigned copending U.S. patent applications Ser. Nos. 08/838,078 and 08/839,614, both filed Apr. 15, 1997, to patent application Ser. No. 08/946,364 filed Oct. 7, 1997, to patent application Ser. No. 09/037,160 filed Mar. 9, 1998 all naming Gordon H. Epstein as first inventor, and to U.S. patent application No. (unknown) filed May 21, 1998 naming Mitchell E. Levinson as first Inventor and entitled "SEALANT APPLICATOR AND METHOD EMPLOYING IMPULSE CLEARING". The disclosures of the aformentioned United States patent applications, "the above applications" are hereby incorporated herein by reference thereto as is the disclosure of provisional application No. 60/102,636 from which the present application claims priority. Continuation status is not being claimed at this time with respect to the aforementioned non-provisional patent applications. This statement is made without prejudice to applicant's right to claim continuation status at any time during copendency of the present application with respect to another application.

STATEMENT REGARDING FEDERALLY SPONSORED RESEARCH OR DEVELOPMENT (Not applicable.)

BACKGROUND OF THE INVENTION

1. Field of the Invention

The present invention relates to an apparatus and method for applying component parts of a sealant which when mixed transforms from a fluidic state to a non-fluidic state. In particular but not exclusively, the present invention is directed to an apparatus and process in which sealant components are mixed prior to being applied to biological tissue to effect hemostasis or achieve other therapeutic results.

2. Description of Related Art Including Information Disclosed under 37 CFR 1.97 and 37 CFR 1.98

Use of tissue sealants and other biological materials is an important emerging surgical technique, well adapted for the operating room or field environments such as the doctor's office or mobile medical units. In addition, the application of such sealants via a catheter provides a non evasive medical technique. Preferred sealants include fibrin sealants which are formed from blood plasma components and comprise, on the one hand, a first component containing fibrinogen and Factor XIII and on the other hand a second component which usually includes thrombin, and calcium ions.

The fibrinogen is capable of a polymerizing and being cross-linked to form a solid fibrin clot when the components are mixed. The necessary additional factors to simulate relevant portions of the natural blood coagulation cascade are suitably distributed between the fibrinogen and thrombin components.

High levels of protection against transmission of infections or induction of immunological reactions can be assured by using an autologous or single-donor source for both components. Such sealants are highly effective, are biologically degraded without residue and may promote wound healing.

Depending upon the potency of the particular formulations employed, coagulation of the sealant may take place very rapidly, yielding a gel within perhaps 10 or 20 seconds after mixing of the two components. Though often very desirable for surgical reasons, such fast-acting properties present potential problems of fouling or clogging. These problems must be overcome in devising suitable applicators, and methods of application.

A popular manually operable applicator for such two-component sealants employs a dual syringe construction wherein two syringes, connected by a yoke, each provide a reservoir for one of the components. In most prior devices, the sealant components are discharged in separate streams and mixed externally of the applicator. Such applicators are similar in principle to household epoxy glue applicators commonly available in hardware stores. Achieving effective mixing externally of the applicator is problematic.

In U.S. Pat. No. 5, 266,877, and the above applications, the present inventor teaches various constructions of a dual syringe applicator wherein the fluid sealant components are mixed internally.

Antanavich et al. U.S. Pat. No. 5,585,007, whose disclosure and references are hereby incorporated herein by reference thereto, provides an extensive discussion of the literature relating to fibrinogen sealant preparation (column 1, line 20 to column 4, line 62) and applicators column 4 line 62 to column 5, line 14), as well as a bibliography, (columns 6–10) and is a helpful guide to the teachings of prior workers in the field.

In one or more of the above copending applications the possibility of retrograde clearing of the mixed fluids pathway within the applicator, using suction, is also disclosed. The applicator is provided with suitable suction conduits and valving to apply suction to the work surface, to prepare it for the application of sealant, for example by removing fluids. As taught, the valving is operable to effect retrograde clearing of a sealant dispensing pathway. Enhanced mixing is possible for example, by impingement and problems of fouling by deposited solids are avoided.

Such applicators, and methods, are remarkably effective for applying sealants to exposed biological surfaces. However, it would be desirable to provide a surgeon, or other user, with additional choices, for example, an applicator and method that could effectively apply sealant to internal biological locations.

One difficulty is that the coagulating nature of the sealants causes the discharge opening or openings of an application device to become clogged so that flow out of the applicator slows down or stops.

While the above-referenced copending applications disclose effective clearing-enabled sealant application devices and methods, their techniques are generally intended for application of sealant to exposed and accessible work surfaces.

There is accordingly a need for a sealant applicator and method that can be used to reach an unexposed or inaccessible location.

SUMMARY OF THE INVENTION

The present invention solves this problem by providing a sealant applicator comprising a dual catheter communicating with fluid sealant agent sources, for example, two internal reservoirs, which sealant applicator can effectively deliver multiple sealant components to a remote tip of the catheter for mixing and dispensing to an area of application.

Preferably this catheter is a dual catheter having one catheter movably mounted with respect to another, for example longitudinally within the other. The movable catheter is then used as a plunger to unclog the openings.

The present invention enables an effective sealant composition to reach an area of application by mixing the sealant components to application or contact with the work surface and providing for removal of coagulated sealant.

Preferably, although not necessarily, the sealant is a biological sealant, for example a tissue adhesive, and the area of application is a biological tissue subject to surgery. The sealant components can comprise a first, structural component capable of gelling, and preferably of solidification and a second, activation component which activates such gelling and, optionally, solidification. More preferably, the sealant is a tissue sealant and the first component comprises fibrinogen and the second component comprises, or can generate a fibrinogen activator, especially thrombin or an equivalent thereof.

The invention also provides a novel surgical method of applying sealant to unexposed or internal biological surfaces, e.g. human or animal anatomical surfaces, that are accessible to a catheter. The use of a dual catheter, which receives a flow of multiple sealant components and mixes the sealant components at the distal end of the catheter, allows the distal end of the catheter to apply a mixed sealant a work site.

BRIEF DESCRIPTION OF THE DRAWINGS

One way of carrying out the invention is described in detail below with reference to the drawings which illustrate one or more specific embodiments of the invention and in which:

FIG. 3b is a cross sectional view along the lines 3b—3b of FIG. 3a;

FIG. 9 is a perspective view of a component part of the present invention;

FIGS. 10 and 10a are a cross sectional view illustrating an alternative embodiment of the present invention;

FIGS. 11 and 11a are a cross sectional view illustrating an alternative embodiment of the present invention;

FIG. 12 is a cross sectional view illustrating an alternative embodiment of the present invention;

DESCRIPTION OF THE PREFERRED EMBODIMENTS

Figure 1:
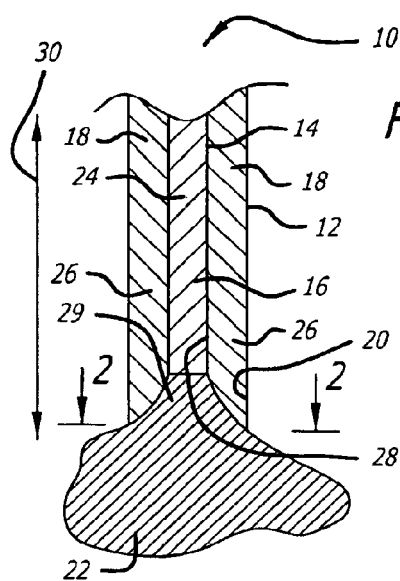
FIG. 1 is a cross sectional elevational view of a catheter sealant applicator according to the present invention.
Figure 2:
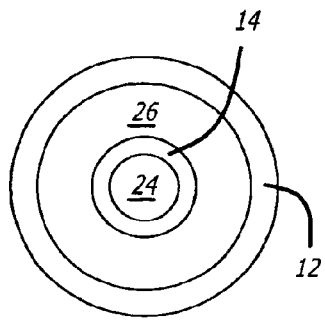
FIG. 2 is a complete bottom view along lines 2—2 of FIG. 1.

Referring now to FIGS. 1 and 2, a sealant applicator 10 is illustrated. Applicator 10 comprises a pair of inner and outer coaxial catheters 12 and 14. In the preferred embodiment inner and outer catheters 12 and 14 are elongated tubes. Inner and outer catheters 12 and 14 are constructed out of any suitable, preferably sterilizable material, for example, stainless steel or polypropylene, and may be rigid or flexible, or may comprise both rigid and flexible components along their lengths. Typically, catheters are substantially longer than the dispensing cannulas described in preferred embodiments of the parent application, having, for example, a length of at least 10 cm, often at least 20 cm and sometimes being substantially longer, for example a meter or more. Commonly, catheters are flexible, or have a flexible portion.

Inner catheter 14 defines an area 16 and is of a smaller diameter than outer catheter 12, this allows outer catheter 12 to surround inner catheter 14 leaving a second area 18.

Outer catheter 12 is configured to have an opening 20 for dispersing a mixed sealant 22.

Sealant 22 is typically comprised of a first sealant agent or component 24 and a second agent or component 26. Component 24 is contained within area 16 and component 26 is contained with area 18. Inner catheter 14 has an opening 28 for discharge of component 24, and in the position shown in FIG. 1 is retracted behind opening 20 of outer catheter 12 to provide a mixing volume 29.

In the preferred embodiment areas 16 and 18 and their respective ratios are of such a configuration as to provide desired proportions of components 24 and 26 to provide a sealant 22 in accordance with the required parameters. As may be desired, areas 16 and 18 and their corresponding volumes may be varied to provide a sealant 22 of various characteristics. For instance, a sealant that may require a longer time to cure or a sealant that may require lesser time to cure by using a lesser or greater proportion or concentration of activator, e.g. thrombin for a fibrinogen sealant.

Areas 16 and 18 are of sufficient size to allow for unimpeded flow of the sealant components.

Inner catheter 14 is slidably or otherwise movably mounted with respect to outer catheter 12 to permit relative movement of inner catheter 14 in the directions of arrow 30.

Figure 3A:
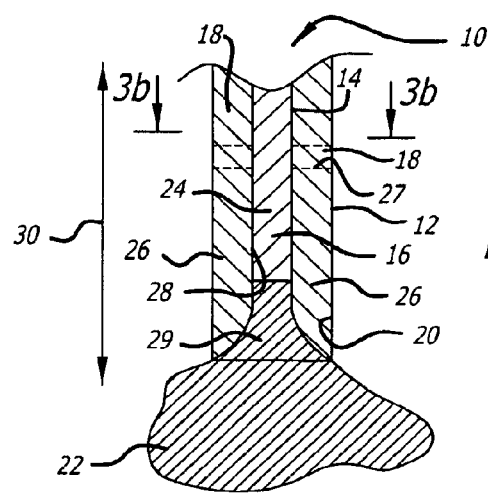
FIG. 3a is a view similar to FIG. 1 illustrating operation of the applicator of the present invention.

The movement of outer catheter 12 allows opening 28 of inner catheter 14 to be positioned within outer catheter 12 and away from opening 20. This position allows components 24 and 26 to mix in an area in close proximity to opening 20. Moreover, and as illustrated in FIG. 3a, the position of opening 28 may be further retracted with respect to outer catheter 12. This positioning will provide a larger mixing volume 29 allowing for a longer mixing time of component 24 and 26.

Alternatively, opening 28 may be positioned closer to opening 20, if desired, to reduce the volume of mixing volume 29 and the time components 24 and 26 are in contact with each other inside applicator 10. This may be appropriate for a very fast setting sealant.

To stabilize inner catheter 14 and maintain the appropriate mixing volumes of components 24 and 26, a stabilizing ring 27 (as illustrated by the dashed lines in FIG. 3a) or the equivalent thereof can be affixed to inner catheter 14 and extend outwardly to outer catheter 12. Stabilizing ring 27 provides stability to inner catheter 14 and is configured to allow component 26 to flow through the same.

Alternatively, and depending on the length of catheters 12 and 14, a plurality of stabilizing rings 27 may positioned within applicator 10 to provide stability to inner catheter 14.

Figure 4:
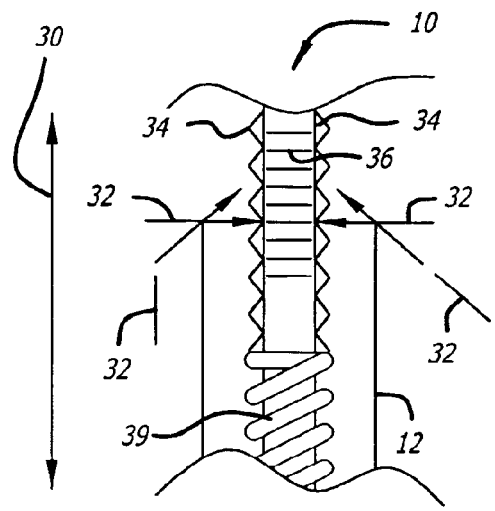
FIG. 4 is a cross sectional elevational of an alternative embodiment of the present invention.

The movement of inner catheter 14 may be effected by any suitable mechanism for example, a proximally located ratchet and pawl mechanism as illustrated in FIG. 4. In this embodiment a locking mechanism 32 restricts the movement of the proximal end of inner catheter 14 by engaging with a plurality of nubs 34. Movement of mechanism 32 into a position, as illustrated by the dashed lines in FIG. 4 will once more allow inner catheter 14 to move in the direction of arrow 30. Mechanism 32 may be configured to have a conveniently placed trigger to facilitate the release.

In addition, and as an alternative, mechanism 32 can work in conjunction with a return spring 39 which is depressed as inner catheter 14 is depressed. Accordingly, as mechanism 32 is released the force of spring 39 acts to return inner catheter 14 to its original position.

Optionally, inner catheter 14 may be provided with graduated markings 36. Markings 36 can indicate the relative position of opening 28 of inner catheter 14 with respect to opening 20 of outer catheter 12. For instance, a marking of zero would indicate that opening 28 and opening 20 are flush with each other. Other markings such as +1,+2,+3, or −1, −2, −3 would indicate the respective location of opening 28 with respect to 20.

In yet another embodiment markings 36 can indicate the flow output of sealant 22 depending on the position of opening 28. Depending on the size of catheters 12 and 14, markings 36 can be configured to indicate flow output of mixed sealant 22, such as millimeters per second or any other suitable indicator of flow output. In addition, markings 36 may also be configured to refer to the mixture ratio of component 24 with respect to component 26.

The movement of inner catheter 14 with respect to outer catheter 12 also allows a user to conveniently purge any clot of hardened sealant 22 from opening 20, as will now be further explained.

Figure 5:
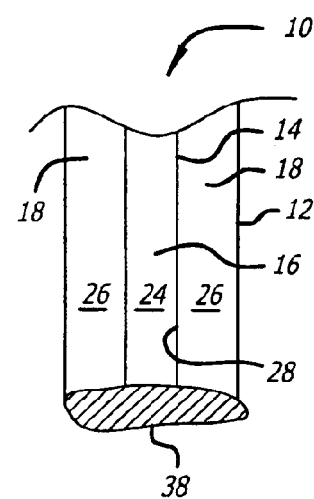
FIG. 5 is a cross sectional view illustrating operation of the present invention.
Figure 6:
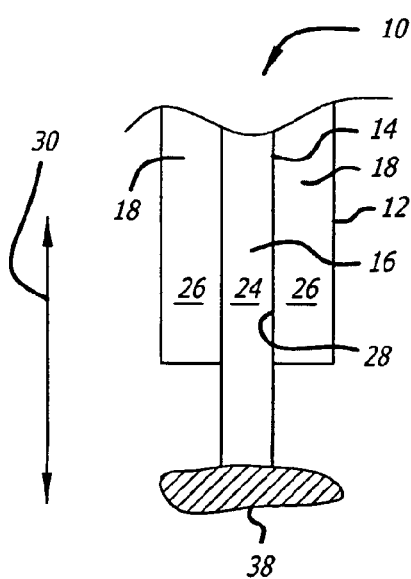
FIG. 6 is a cross sectional view illustrating operation of the present invention.

Turning now to FIGS. 5 and 6, and as previously discussed the internal mixing of components 24 and 26 effects coagulation of sealant 22. However, such coagulation may cause a clot 38 to block opening 20. This problem is addressed by the mobility of inner catheter 14. To facilitate the removal of clot 38 the user can simply move inner catheter 14 to the position illustrated in FIG. 6. Such movement may be accomplished through the use of a trigger mechanism as described with reference to FIG. 4, or any other suitable mechanism.

Figure 3B:
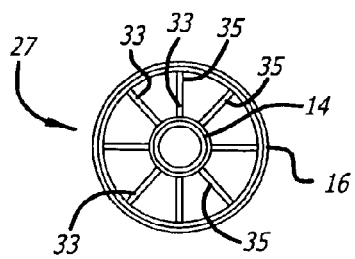

In yet another embodiment stabilizing ring 27 (FIGS. 3a and 3b) is also used as a plunger for removal of clot 38. In this embodiment stabilizing ring 27 is slidably mounted in area 18 positioned between inner catheter 14 and outer catheter 12. Movement of ring 27 is effected through the use of a user manipulated trigger mechanism. To remove clot 38 the user simply causes ring 27 to move towards opening 20. Such movement will dislodge clot 38. As an alternative, a plurality of stabilizing rings 27 may be positioned throughout area 18.

Stabilizing ring 27 allows component 26 to flow through area 18 unimpeded, however, stabilizing ring 27 is constructed in such a manner as to force clot 38 from opening 20 once stabilizing ring 27 has made contact with clot 38.

One such configuration is that of a spoked wheel (FIG. 3b) wherein the spokes 33 of stabilizing ring or rings 27 define a plurality of openings 35. Openings 35 are large enough to allow component 26 to pass through while being small enough to force the removal of clot 38.

Figure 3C:
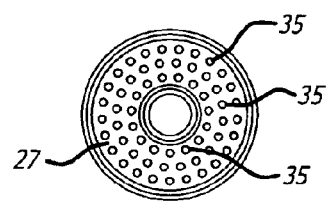
FIG. 3c is a cross sectional view of an alternative embodiment of the present invention.

Alternatively, ring or rings 27 is a disk having a plurality of smaller openings 35 (FIG. 3c).

Movement of stabilizing ring 27 is effected through the use of a trigger mechanism, such as a plunger or the equivalent thereof, positioned at the proximal end of applicator 10 which is conveniently accessed by the user's finger or thumb.

In yet another embodiment, ring or rings 27 are secured to inner catheter 14. Thus, as the user manipulates or moves inner catheter 14 ring 27 also moves.

In a still further embodiment, rings 27, or inner catheter 14 with rings 27 secured to it, are capable of being rotated as they are being depressed. Such rotation will enhance the dislodging of clot 38.

Figure 7:
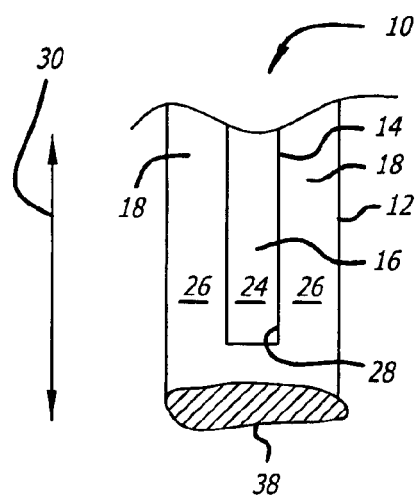
FIG. 7 is a cross sectional view illustrating operation of the present invention.
Figure 8:
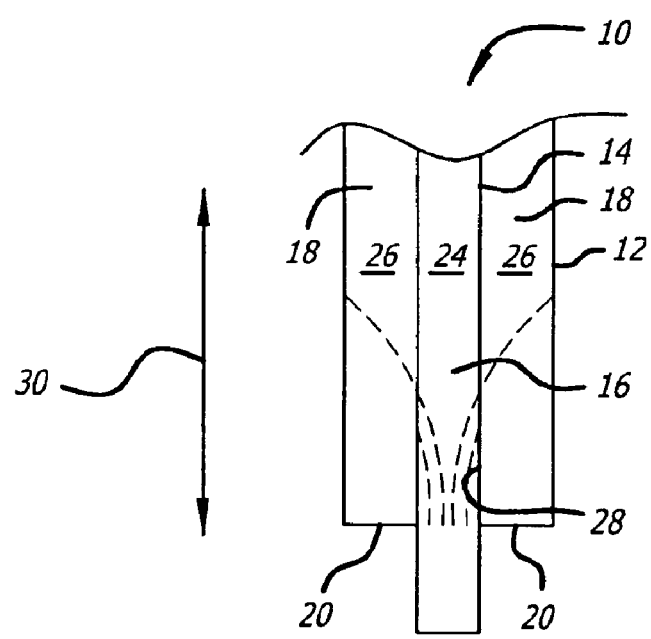
FIG. 8 is a cross sectional view illustrating operation of the present invention.
Figure 8:
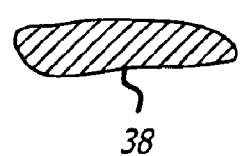

Other clot removal techniques such as those illustrated in FIGS. 7 and 8 may be utilized. In this sequence, a user first moves inner catheter 14 into the position illustrated in FIG. 7. The movement will dislodge clot 38 from opening 28 of inner catheter 14. Then the user moves inner catheter 14 into the position illustrated in FIG. 8. This movement allows inner catheter 14 to act as a plunger which will dislodge clot 38 from opening 20 thereby discharging clot 38 from applicator 10.

Alternatively, and as illustrated by the dashed lines in FIG. 8, catheters 12 and 14 may be constructed out of a flexible material capable of being manipulated into the squeezed position illustrated by the dashed lines. This configuration allows the distal end of applicator 10 to be compressed to dislodge clot 38. In addition, small amounts of components 24 and 26 will be forcibly dispelled during this compression and will aid in the clearing of applicator 10. The manipulation of applicator 10 can be performed by the fingers of the user or a pinching mechanism which could be hand held or adhered to applicator 10.

Alternatively, catheters 12 and 14 may be constructed out of a flexible material capable of be manipulated at the proximal end of applicator 10 to effectively pinch off the supply of components 26 and 24. The compression of catheters 12 and 14 at the proximal end also causes small amounts of components 24 and 26 to be discharged. Such placement of a pinching mechanism or pinching capability at the proximal end of applicator 10 also provides for an ergonomic device.

Openings 28 and 20 may be equipped with a closing mechanism, such as a removable cover 31 (illustrated in FIG. 9) which prevents unrestricted flow of components 24 and 26 from inner and outer catheters 12 and 14 between uses.

Referring now to FIGS. 10 and 10a an alternative embodiment of the present invention is illustrated. In this embodiment, components and/or parts performing analogous or similar functions are numbered in multiples of 100. Here an opening or plurality of openings 128 are positioned along the elongated portions or walls of catheter 114. These openings allow component 124 to mix with component 126 throughout an extended mixing volume 129 prior to discharge of mixed sealant 122 from opening 120. This embodiment allows for a particularly effective mixing of components 124 and 126 prior to application.

In this embodiment the end of catheter 114 is closed. Accordingly, mixed sealant 122 is applied to the required location through opening 120. Catheter 114 may also be positioned to apply sealant 122 as illustrated in FIGS. 11 and 11*a*.

In the case where a clot 138 has blocked opening 120, catheter 114 may also be used as a plunger to remove clot 138 (as illustrated by the dashed lines in FIG. 11*a*).

In yet another embodiment, and as illustrated in FIG. 12, catheter 214 is configured to have a plurality of smaller openings 228 throughout a selected length of the distal end of the catheter 214, for example 1 or 2 cm., or the entire surface of catheter 214. This configuration allows for an even greater mixing volume 229. Preferably, sufficient pressure of sealant agent or component is maintained in inner catheter 214 to ensure avoid possible backflow and clogging of openings 228 owing to mixing of the sealant components in the openings.

In addition and in order to aid in the clot expulsion as depicted in FIGS. 6–8 small amounts of components 24 and 26 may also be expelled with the clot to ensure that all of the clot is removed from applicator 10.

Figure 13:
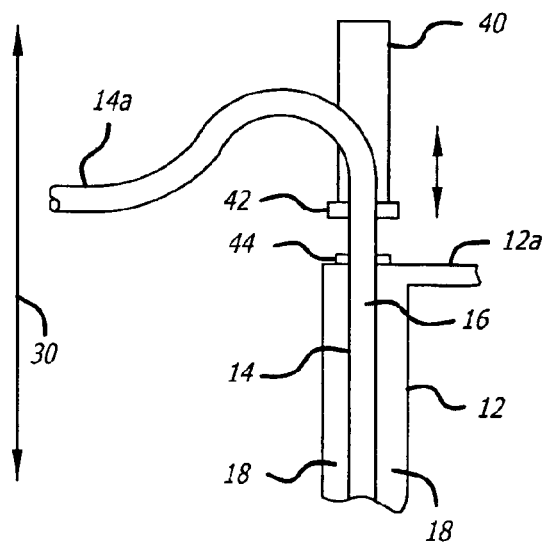
FIG. 13 is a cross sectional view illustrating an alternative embodiment of the present invention.

Referring now to FIG. 13, one possible supply connection of inner and outer catheters 12 and 14 is illustrated. A flexible connector 14*a* is connected to the proximal end of inner catheter 14. Flexible connector 14*a* supplies area 16 with sealant component 24. The flexible nature of connector 14*a* allows inner catheter 14 to move in the directions of arrow 30.

Movement of inner catheter 14 is facilitated by the manipulation of an actuating mechanism 40 which is secured to inner catheter 14 via a clamping device 42. Such manipulation causes a corresponding movement of inner catheter 14, and may be effected by a manual control (not shown), for example a spring-loaded depressible button or trigger.

A flexible gasket 44 allows for movement of inner catheter 14 while providing a secure seal around catheters 14 and 12.

Outer catheter 12 is also connected to a connector 12*a*. Connector 12*a* supplies area 18 with sealant component 26. Connector 12*a* may also be flexible, however connector 12*a* may be constructed out of a more rigid material.

Figure 14:
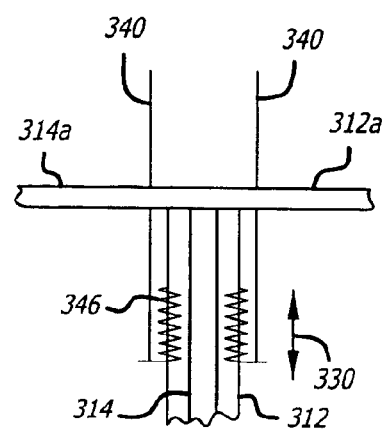
FIG. 14 is a cross sectional view illustrating an alternative embodiment of the present invention.

Referring now to FIG. 14 yet another alternative embodiment of the supply connection of the present invention is illustrated Here both inner and outer catheters 314 and 312 are connected to connectors 312*a* and 314*a*. In this embodiment catheter 312 is configured to have a flexible and expansible portion 346, which can, for example, be of fanfold or accordion-like bellows construction and is located intermediate to catheter 312 and connector 312*a*. Flexible portion 346 allows for constriction and expansion of outer catheter 312 in the directions depicted by arrow 330. Movement of catheter 312 is effectuated by an actuating mechanism 340. As mechanism 340 advances or retracts catheter 312 also moves in the same direction.

Figure 15:
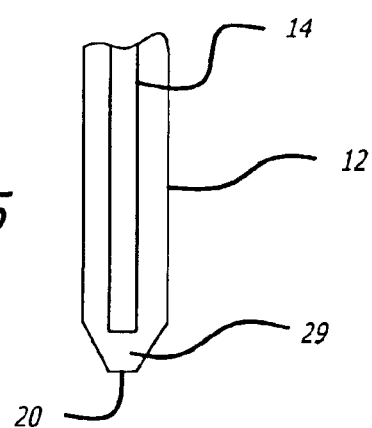
FIG. 15 is a cross sectional view illustrating an alternative embodiment of the present invention.

Referring now to FIG. 15 an alternative embodiment of the distal, delivery end of applicator 10 is illustrated. Here catheter 12 is configured to have a tapered end, constricting the flow of sealant components to provide a mixing volume 29 with strong turbulence. The outer diameter of inner catheter 14 can be as large as opening 20, thus when inner catheter 14 is advanced, it exerts a precise plug-removal clearing action on the reduced diameter tip of outer catheter 12.

Figure 16:
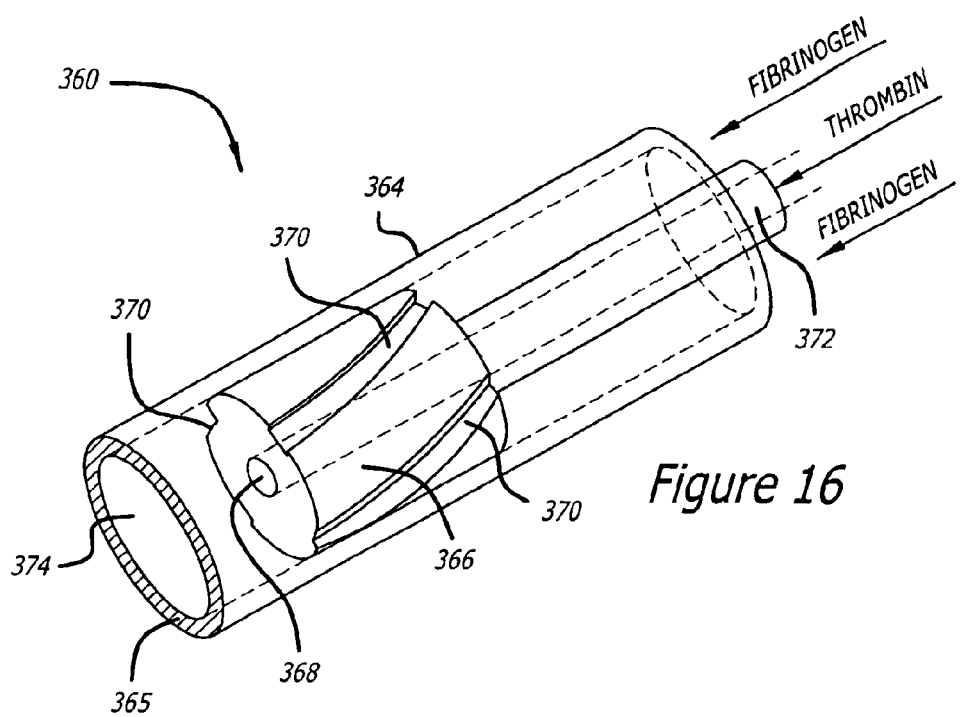
FIG. 16 is a perspective view of a further embodiment of the invention employing a plug-like inner catheter, in a retracted position within an outer catheter shown as being transparent to reveal the inner structure.
Figure 17:
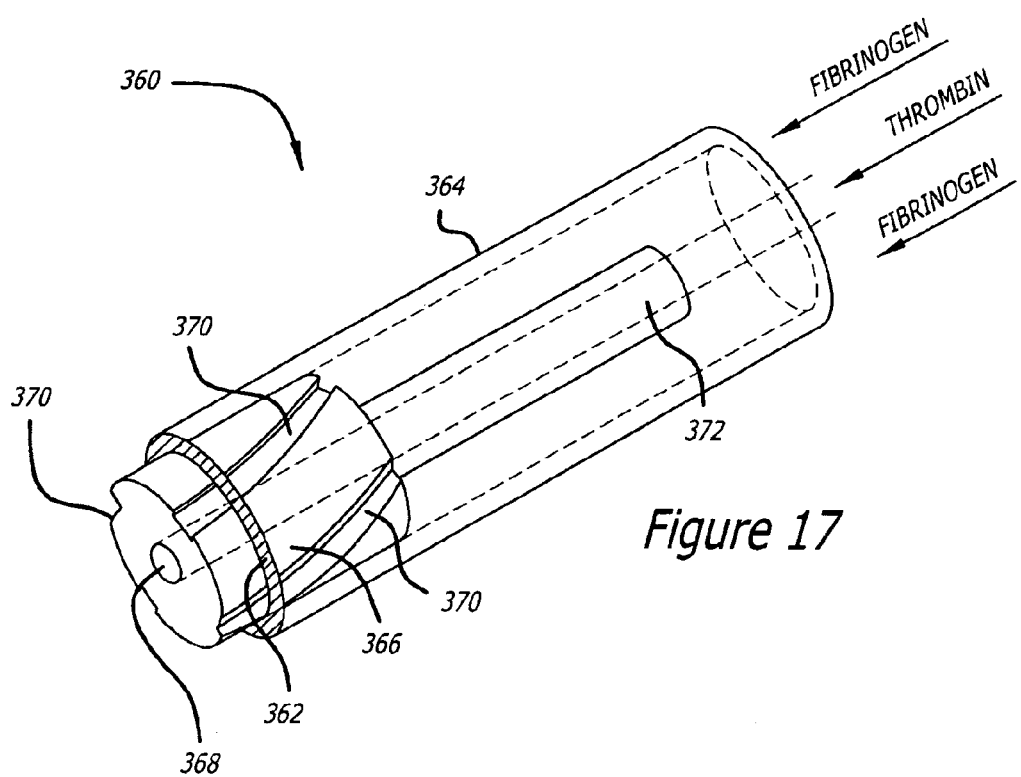
FIG. 17 is a view similar to FIG. 16 with the plug-like inner catheter in an advanced position.

The embodiment of the invention shown in FIGS. 16-17, comprises a modified clearing-enabled, dual catheter sealant applicator 360 which can be fabricated from suitably soft or resilient materials, to have a flexible or malleable end or tip 362 to facilitate or enhance engagement of the applicator with, and entry of the applicator into, living tissues, for example, the ear, the nose or the throat. The material of applicator 360, at least at tip 362, should preferably be sterilizable and non-absorbent, as well as soft, or deformable, and resilient, and may for example, be a silicone rubber.

Catheter sealant applicator 360 comprises a hollow outer sheath 364, an inner plug 366 which has an axial bore 368 and external channels 370, and a supply lumen 372 press-fitted into plug 366. As shown, four symmetrically disposed channels 370 are provided, but other numbers of channels 370 such as three, six or eight may be employed. The outer diameter of plug 366 is a close sliding fit within the inner diameter of sheath 364. The cross-sectional areas of channels 370 and bore 368 are selected to provide desired relative flow rates of sealant agents, which relative flow rates may be varied, or selected, by using plugs 366 of different configurations. Such diverse plugs 366 may be supplied each with a lumen 372, or may be interchangeably fittable to one or more lumens 372. Optionally, channels 370 on plug 366 can taper outwardly, in the fluid delivery direction, which is to say distally, to increase the channel area in the direction of flow and facilitate clearing and the removal of clots.

A further option is for channels 370 to have a helical configuration, as shown, simulating rifling, to impart spin to the fluid travel to enhance mixing of the sealant agents. In such case a still further option is for channels 370 to be twisted in opposed directions around plug 366, to impart countercurrent flows and further enhance mixing.

Preferably, the sealant catalyst, for example, in the case of a fibrinogen sealant, thrombin or other fibrinogen activator, is supplied through lumen 372 to bore 368 in plug 366, and fibrinogen or other polymerizable sealant agent, is supplied in the space between the outside of the lumen and the inside diameter 374 of sheath 364.

For application of sealant, the forward or distal face of plug 366 is slightly retracted behind the distal end of sheath 364 to allow mixing of the two agents to take place in a mixing volume disposed generally within the sheath 364. As with other embodiments described herein, significant mixing of the sealant components takes place before delivery of the sealant agents to, or contact of the sealant agents with, the target work surface.

Once a cycle of sealant application is complete, tip 362 can be cleared of any clot or other material, by advancing lumen 372, driving plug 366 forwardly inside sheath 364 and expelling the clot. If necessary, the clot can be freed from the face of plug 366, or loosened, by dispensing a small amount of sealant.

The invention provides a novel surgical method of applying sealant to unexposed or internal biological surfaces, e.g. human or animal anatomical surfaces, that are accessible to a catheter, for example, inner ear structures, the veins and arteries and organs such as the heart that are accessible via veins and arteries, the bladder, and so on. The method comprises use of a dual catheter such as described hereinabove, which is coupled to a sealant applicator to receive a flow of multiple sealant components from the applicator and to mix the sealant components at the distal end of the catheter, and insertion of the catheter into a body organ to advance the distal end of the catheter to a work site, operation of the sealant applicator to dispense sealant from the distal end of the dual catheter, and removal of the dual catheter from the body organ. After removal, the tip of the dual catheter will usually be cleared of any clog by operating the inner catheter as a plunger and ejecting the clog to waste. In an exceptional case, and with due care on the part of the surgeon or other operator, the inner catheter may be advanced while the dual catheter is inserted into a body organ, to free the dual or outer catheter, or clear and obstruction or, possibly, to manipulate the work surface.

While illustrative embodiments of the invention have been described above, it is, of course, understood that various modifications will be apparent to those of ordinary skill in the art. Many such modifications are contemplated as being within the spirit and scope of the invention.

What is claimed is:

1. A multi-component sealant applicator, comprising:

a dual catheter for delivering sealant, each catheter communicating with one of a pair of fluid sealant agent sources;

a mixing volume within the dual catheter for mixing multiple components of a multi-component sealant prior to discharge from a distal end of the catheter; and a clearing system to clear undesired material from the mixing volume or the vicinity of the mixing volume, wherein one catheter is mounted for longitudinal movement within the other and the inner catheter is usable as a plunger to remove clogs.

2. A multi-component sealant applicator comprising:

a dual catheter for delivering sealant, each catheter communicating with one of a pair of fluid sealant agent sources;

a mixing volume within the catheter for mixing components of a multi-component sealant prior to discharge from a distal end of the catheter; and a reciprocal drive mechanism proximally coupled with the dual catheter to move one catheter longitudinally with respect to the other.

3. A multi-component sealant applicator comprising:

a dual catheter for delivering sealant, each catheter communicating with one of a pair of fluid sealant agent sources;

a mixing volume within the catheter for mixing components of a multi-component sealant prior to discharge from a distal end of the catheter; and a reciprocal drive mechanism proximally coupled with the dual catheter to move one catheter longitudinally with respect to the other, the drive mechanism comprising a ratchet and pawl.

4. A multi-component sealant applicator comprising:

a dual catheter for delivering sealant, each catheter communicating with one of a pair of fluid sealant agent sources, wherein the proximal ends of the catheter are coupled to sources of sealant components, one catheter being coupled through a flexible gasket allowing for relative movement of the catheters and providing a fluid seal; and a mixing volume within the catheter for mixing components of a multi-component sealant prior to discharge from a distal end of the catheter.

* * * * *